United States Patent [19]

Mazid et al.

[11] Patent Number: 5,308,460
[45] Date of Patent: May 3, 1994

[54] RAPID SYNTHESIS AND ANALYSIS OF CARBOHYDRATES

[75] Inventors: M. Abdul Mazid; John C. Klock, both of Novato, Calif.

[73] Assignee: Glyko, Incorporated, Novato, Calif.

[21] Appl. No.: 968,980

[22] Filed: Oct. 30, 1992

[51] Int. Cl.$^5$ .............................................. C25B 3/00
[52] U.S. Cl. .............................. 204/180.1; 204/182.8; 204/299 R; 435/14; 435/18; 435/72
[58] Field of Search ............. 204/180.1, 182.8, 299 R; 435/14, 18, 72

[56] References Cited

U.S. PATENT DOCUMENTS 5,100,778  3/1992  Rademacher et al. ............ 204/182.8
5,205,917  4/1993  Klock, Jr. ......................... 204/180.1

FOREIGN PATENT DOCUMENTS 9211531  7/1992  World Int. Prop. O. .

Primary Examiner—John Niebling
Assistant Examiner—C. Delacroix-Muirheid
Attorney, Agent, or Firm—Albert P. Halluin

[57] ABSTRACT

The subject invention provides novel methods and apparatus for synthesizing carbohydrates of a desired structure. The subject synthesis methods include using carbohydrage-modifying enzymes to perform individual synthesis reaction steps and electrophoresis to purify the reaction products for possible further use as substrates in additional synthesis reactions. The subject invention also provides novel methods and apparatus for detecting carbohydrates of interest. The methods and apparatus for synthesizing or detecting carbohydrates involve the use of carbohydrate-modifying enzymes immobilized in a reaction matrix gel and fluorophore labelled substrates that may be removed from the reaction matrix gel by electrophoresis and subsequently analyzed or transferred to another reaction gel matrix.

The subject invention also provides methods for detecting and quantitating specific carbohydrate-modifying enzymes that might be present in a sample for analysis.

24 Claims, No Drawings

RAPID SYNTHESIS AND ANALYSIS OF CARBOHYDRATES

TECHNICAL FIELD

The invention relates to the field of carbohydrate chemistry. More specifically, the invention concerns enzyme mediated synthesis of carbohydrates, enzyme mediated detection of carbohydrates, and methods for detecting enzymes capable of catalyzing reactions with carbohydrates.

BACKGROUND

There is great interest in the study of biologically active oligosaccharides, mainly because of the appreciation of their potential in biology and medicine. This interest has generated a growing need for methods of efficiently and inexpensively preparing oligosaccharides, particularly for the purpose of studying their biochemical function and assessing their potential in therapeutics or as diagnostic tools. Biologically important oligosaccharides are often difficult to obtain from natural sources in sufficient quantities for any systematic biochemical studies. Even when available from natural sources, it is still important to have independently synthesized oligosaccharides to confirm the structure-activity relationships of the molecules.

Until recently, "glycobiologists" have relied on traditional organic chemical synthesis which remains extremely time consuming, cumbersome, and sometimes prohibitively expensive. The formation of isomeric mixtures in chemical glycosylation reactions, the requirements of multiple protection and deprotection steps, and the tedious task of purification of products have been responsible for their vanishing yields. As an alternative to organic chemical synthesis, the enzymatic synthesis of carbohydrates is a particularly attractive approach because the use of enzymes allows stereospecific synthesis and overcomes some of the other limitations of purely chemical syntheses. Thus the difficult process of oligosaccharide synthesis has been aided by enzymatic catalysis and the combined chemo-enzymatic approach has been increasingly reported in the literature, for example, C. A. Compston, C. Condon, H. R Hanna and M. A. Mazid, Carbohydr. Res., 239: 167–176 (1993). Another recent paper describes an electrophoresis-based assay for glycosyltransferase activity which utilizes fluorophore-labelled carbohydrate substrates K. B. Lee, U. R. Desai, M. M. Palcic, O. Hindsgaul and R. J. Linhardt, Anal. Biochem., 205: 108–114 (1992); however, this method also appears time-consuming, tedious or cumbersome in terms of multiple purification steps and ultimate characterization or quantitation of products by sophisticated analytical techniques such as FAB-MS, NMR and capillary zone electrophoresis. A method of carbohydrate synthesis that would permit the convenient separation of reaction products from enzyme and substrates would be a significant advance over currently available methods of carbohydrate synthesis.

The enzymatically-assisted in vitro synthesis of specific oligosaccharides employs three general strategies. These include the use of glycosyltransferases of the Leloir pathway which require sugar-nucleotides as donors, F. Leloir, Science 172: 1299–1303 (1971); H. Nikaido and W. Z. Hassid, Adv. Carbohydr. Chem. Biochem., 26: 351–483 (1971), the use of non-Leloir pathway enzymes which require sugar-1-phosphate as donors, and the use of glycosidase or glycosylhydrolase-catalyzed reaction for the formation of glycosidic bonds in a kinetic or thermodynamic approach I. Toone, E. S. Simon, M. D. Bednarski and G. M. Whitesides, Tetrahedron, 45: 5365–5422 (1989); S. David, C. Auge and C. Gautheron, Adv. Carbohydr. Chem. Biochem., 49: 175–237 (1991). Several in situ regeneration systems have been reported which avoid the separate tedious preparation of sugar-nucleotides and stoichiometric use of nucleoside mono- and diphosphates that are known inhibitors for the corresponding glycosyltransferases. However, these approaches are generally aimed at the preparative synthesis of oligosaccharides which involve longer purification steps and additional complexities.

The range of carbohydrates that can be produced by a combined chemo-enzymatic approach, particularly synthesis of oligosaccharides, is much greater than simply reproducing the natural biosynthetic reactions for which the enzymes are known to exist. Also, as more glycosyltransferases become available, they could be used to produce a diversity of unnatural oligosaccharides that would be useful in the area of glycoprotein or glycolipid remodelling. M. M. Palcic and O. Hindsgaul, Glycobiology, 1:205–209 (1991). Such studies are extremely important not only for understanding the function of natural glycoconjugates, but also for the design and development of carbohydrate-based therapeutics or diagnostics. However, in order to produce the desired oligosaccharide product, not only must the enzyme and substrates involved in the synthesis be readily available, but suitable techniques for rapidly analyzing and purifying the products should also be available. Conventional synthesis techniques may produce desired oligosaccharides in extremely small quantities, sometimes beyond the detection limit of modern-day sophisticated carbohydrate analytical techniques; thus the lengthy purification steps required to obtain a product of the desired purity often cannot be used successfully. Therefore, traditional approaches for the synthesis and analysis of carbohydrates would appear generally unsuitable to meet most needs of the ordinary glycobiologists.

Conventional methods for the identification, characterization, and synthesis of carbohydrates require lengthy chromatographic separations and the use of sophisticated instruments which are often outside the reach of an ordinary glycobiology laboratory. Hence, it is of interest to provide highly sensitive and convenient methods for the utilization of carbohydrate-modifying enzymes in oligosaccharide synthesis. Such highly sensitive and convenient methods would have a number of uses that are difficult, expensive or impossible, to achieve using currently available techniques. These uses include the detection and purification of carbohydrate products having natural or unnatural structures. For the sake of convenience and economy, it is also of interest to provide for the repeated use of enzyme preparations for carbohydrate synthesis and detection. Furthermore, it is of interest to provide methods of assaying for the presence of carbohydrate-modifying enzymes in a sample for analysis.

SUMMARY OF THE INVENTION

The subject invention provides novel single-step methods and apparatus for synthesizing and purifying carbohydrates of a desired structure. The subject invention also provides novel methods and apparatus for detecting carbohydrates of interest. The subject invention also provides novel methods for detecting carbohydrate-modifying enzymes.

One aspect of the subject invention is to provide methods for the step-wise synthesis of carbohydrates using carbohydrate-modifying enzymes. In these synthesis methods a carbohydrate-modifying enzyme and substrate(s) are incubated together so as to produce a reaction product. The reaction product is subsequently fluorophore labelled. The reaction product is then separated from other components in the reaction mixture by electrophoresis. The separated reaction product may be used as a substrate in additional reactions employing carbohydrate-modifying enzymes so as to provide for repeated rounds of substrate modification. The subject invention also provides apparatus for carrying out carbohydrate synthesis employing carbohydrate-modifying enzymes.

Another aspect of the subject invention is to provide a method of synthesizing carbohydrates by adding a fluorophore-labelled substrate to a reaction matrix gel containing an immobilized carbohydrate-modifying enzyme, incubating the reaction matrix gel containing the substrate, and removing the reaction product by electrophoresis. The carbohydrate-modifying enzyme may be immobilized in the reaction matrix gel by covalent attachment to the reaction matrix or, preferably, by embedding in the reaction matrix gel. The reaction product removed from the reaction matrix gel may be transferred to a second reaction matrix gel containing a different carbohydrate-modifying enzyme so as to provide for additional modifications of the first reaction product. Another aspect of the invention is to provide apparatus for carrying out the subject carbohydrate synthesis methods.

Still another aspect of the subject invention is a method for measuring the presence of a carbohydrate of interest in a sample for analysis. The sample for analysis is added to a reaction matrix gel containing an immobilized carbohydrate-modifying enzyme that is capable of using the carbohydrate of interest as a substrate. Another aspect of the invention is to provide apparatus for carrying out the measurement of the presence of a carbohydrate of interest in a sample for analysis using a reaction matrix gel comprising an immobilized carbohydrate-modifying enzyme capable of using the carbohydrate of interest as a substrate. The subject method and apparatus for measuring carbohydrates in a sample involve the production of a fluorophore-labelled reaction product that is removed from the reaction matrix gel by electrophoresis. The subject invention also provides apparatus for carrying out the subject carbohydrate detection methods.

Another aspect of the subject invention is a method for detecting compounds, especially enzymes, with carbohydrate-modifying activity. This method involves the step of mixing a substrate or substrates with a solution suspected of containing a compound with carbohydrate-modifying activity. The substrate may be labelled with a fluorophore prior to the mixing step; alternatively, the reaction mixture may be treated with a fluorophore so as to label all carbohydrates present. After the mixing step, fluorophore assisted carbohydrate electrophoresis is applied so as to separate labelled carbohydrates in the reaction mixture.

DESCRIPTION OF THE SPECIFIC EMBODIMENTS Definitions

The term "reaction matrix" as used herein refers to a network of polymeric molecules that constitute the non-liquid component of a gel. Similarly, the term "reaction matrix gel" refers to a gel that has a reaction matrix as the solid component. Examples of "reaction matrix" and "reaction matrix gels" include polyacrylamide, agarose, dextran, cellulose, polystyrene, poly(N-tris[hydroxymethyl]methyl methacrylamide), and the like. One or more carbohydrate-modifying enzymes may be covalently attached to the "reaction matrix", either directly or indirectly, i.e., through the use of spacer arms and cross-linking reagents. The reaction matrix may be used to form a gel after being solvated by any of a number of liquids, particularly aqueous buffer solutions. Enzymes may be embedded within a reaction matrix gel. A reaction matrix gel may be used as a resolving gel for electrophoresis.

The term "immobilized" and "immobilize" as used herein refer to the fixation of an enzyme to a reaction matrix gel so as to prevent or reduce the diffusion of the enzyme(s) of interest from the reaction matrix gel. An enzyme may be "immobilized" by covalently binding the enzyme directly to the reaction matrix through covalent interactions between the matrix and various substituent groups on the enzyme of interest. Similarly, an enzyme may be immobilized by covalently binding the enzyme to the reaction matrix through various cross-linking reagents and spacer arms. Preferably, enzymes of interest may be immobilized in a reaction matrix gel by "embedding" the enzyme in the reaction matrix. The term "embedding" when used in reference to immobilizing an enzyme in a reaction matrix gel refers to placing the enzyme in the liquid phase of a reaction matrix gel formed by the reaction matrix and the liquid phase. Although an enzyme that has been "embedded" in a reaction matrix gel is not covalently bound to the matrix, the reaction matrix limits the free diffusion of the enzyme so as to significantly retard the ability of the enzyme of interest to diffuse out of the reaction matrix gel.

The terms "incubating" and "incubation" as used herein refers to the acts of allowing time for a enzymatic reaction to take place. The step of "incubation" may be the same step as the step of mixing the components, i.e., enzyme and substrate(s), of the reaction. "Incubation" may also take place before or concomitantly with electrophoresis in the subject methods and apparatus.

The term "substrate" when used without qualifiers refers to molecules undergoing a chemical reaction catalyzed by a carbohydrate-modifying enzyme. A chemical reaction catalyzed by a carbohydrate-modifying enzyme may involve one or more substrates.

The term "carbohydrate-modifying enzyme" as used herein refers to enzymes that can catalyze a chemical reaction wherein at least one of the reactants is a carbohydrate. It will be appreciated by the person of average skill in the art of biochemistry or organic chemistry that molecules capable of mediating carbohydrate-modifying reactions that are not carbohydrate enzymes may, in certain circumstances, be used in place of, or in conjunction with carbohydrate modifying enzymes. These other molecules may include lectins, antibodies (abzymes), organic and inorganic compounds, and a variety of proteins not traditionally considered enzymes but capable of acting similarly to enzymes, e.g., lactalbumin in lactose synthesis. The term "enzymes" as used herein refers to carbohydrate-modifying enzymes, unless indicated otherwise. Carbohydrate-modifying enzymes may alter the structure of the substrate carbohydrates in a variety of ways, including the reverse hydrolysis of linkages between saccharide units (transglycosidation by hydrolases), the formation of new linkages between saccharide units by glycosyltransferases, and the addition of various side groups to carbohydrate molecules. Carbohydrate-modifying enzymes include hydrolases, lyases, acetylases, sulfatases, phosphatases, kinases, epimerases, methylases, amidases, transferases, and the like. Carbohydrate-modifying enzymes are said to have a "carbohydrate-modifying activity." The term "carbohydrate-modifying activity" refers to the reactions catalyzed by the carbohydrate-modifying enzyme of interest.

The term "measuring" and "measure" as used herein refers to both the quantitative and qualitative determination of the amount of a given compound in a sample of interest.

THE INVENTION

The subject invention provides methods for conveniently synthesizing carbohydrates of interest and apparatus for carrying out these synthesis methods. A novel aspect of the invention is that synthesis of a carbohydrate reaction product and separation of the reaction product from the precursor reactants is achieved in single steps, thus increasing the speed and ease with which synthesis may be achieved. Additionally, the subject invention provides for methods of measuring the presence (or absence) of carbohydrates of interest in test samples, and also provides for apparatus employing these methods to measure the presence of carbohydrates of interest. Some embodiments of the methods and apparatus provided may use carbohydrate-modifying enzymes immobilized in a reaction matrix gel for carrying out reaction synthesis step(s) or for detecting carbohydrates in a sample for analysis.

The subject invention has numerous advantages over conventional methods of synthesizing carbohydrates. One advantage of the invention is the ease with which carbohydrates may be synthesized; prior carbohydrate synthesis techniques required the use of difficult chromatographic techniques. Another advantage of the invention is that carbohydrates may be synthesized on a scale that is significantly smaller than possible with conventional organic chemistry carbohydrate synthesis.

Carbohydrates of interest may be produced by employing a series of synthesis steps utilizing carbohydrate-modifying enzymes so as to obtain the desired carbohydrate product or products. By employing carbohydrate-modifying enzymes of known enzymatic activity, the person of average skill in the art may design a series of enzymatic reactions for the synthesis of a particular carbohydrate or carbohydrates. References describing various carbohydrate-modifying enzymes and their biological activity can be found, among other places, in *Methods in Enzymology*, volumes 179, 138, 83, 50, 28 and 8 (Complex Carbohydrates), Academic Press, San Diego, Calif., and *The Enzymes*, Boyer, editor. Each carbohydrate-modifying enzyme in the series required for synthesis is said to catalyze a "synthesis reaction step."

Carbohydrates of a desired structure may be produced through enzymatic synthesis by adding a substrate(s), either pre-labelled or not pre-labelled with a fluorophore, and a carbohydrate-modifying enzyme that catalyzes the synthesis reaction step of interest so as to form a reaction mixture. After the reaction mixture has been allowed to incubate, the carbohydrates in the reaction mix are subjected to fluorophore-assisted carbohydrate electrophoresis so as to isolate the desired reaction product. The isolated reaction product may then be used as a substrate in a second reaction catalyzed by a second carbohydrate-modifying enzyme. The second reaction mixture may include a carbohydrate-modifying enzyme that is the same or different from the carbohydrate-modifying enzyme used in the first reaction. The second reaction mixture may also include substrates that are present or not present in the first reaction mixture. The process may then be repeated with different carbohydrate-modifying enzymes and substrates so as to produce the desired carbohydrate.

The technique of fluorophore assisted carbohydrate electrophoresis is employed to purify the reaction product of the reactions catalyzed by the various carbohydrate-modifying enzyme employed during the synthesis of a carbohydrate of interest. The technique of fluorophore assisted carbohydrate electrophoresis is described in detail in U.S. Pat. No. 4,874,492, U.S. patent application Ser. No. 07/317,480, filed Feb. 14, 1989, P. Jackson, *Biochem. Journal*, 270:705-713 (1990), and P. Jackson, *Anal. Biochem.*, 196:238-244 (1991). Fluorophore-assisted carbohydrate electrophoresis permits the electrophoretic separation of a complex mixture of carbohydrates into distinct bands on a gel. Prior to electrophoresis, a carbohydrate mixture for analysis is treated with a charged fluorescent tag that combines with the reducing end of the carbohydrates for analysis. The fluorescent label permits the quantitative measurement of the labelled carbohydrates. The charged tag not only fluorescently labels the carbohydrates, but imparts an ionic charge, thus permitting hitherto uncharged carbohydrates to migrate in an electric field. After the carbohydrates have been labelled, the sample is subjected to polyacrylamide gel electrophoresis, or related separation techniques, in order to separate and concentrate the labelled carbohydrates into bands. The separated carbohydrates may be visualized directly by fluorescence under U.V. light. Alternatively the separated carbohydrates may be visualized by means of laser-scanner photomultiplier tube system, a charge coupled device (CCD). CCDs are semiconductor imaging devices that permit the sensitive detection of emitted light. CCDs and their uses are described in U.S. Pat. Nos. 4,874,492 and 4,892,137. The image produced by the CCD may be subsequently transferred to a computer wherein the bands may be analyzed with the respect to parameters such as intensity, mobility, migration distance, and the like.

The carbohydrate reaction products purified by fluorophore assisted carbohydrate electrophoresis may be removed from electrophoresis gel by a variety of methods. These methods include: continued electrophoresis of bands until they leave the gel, electroblotting, excision of gel containing the band with dialysis, and the like.

The structure of the substrates used in carbohydrate synthesis will vary in accordance with the identity of the carbohydrate-modifying enzymes used and with the identity of the desired synthesis product. The substrates are selected so as to be capable of being structurally altered by the carbohydrate-modifying enzyme. Substrates to be included in a synthesis reaction step or the reaction products of individual synthesis reaction steps may be fluorophore labelled so as to provide for the separation of the reaction products of individual synthesis reaction steps by fluorophore assisted carbohydrate electrophoresis. Preferably, reaction products are fluorophore labelled rather than substrates, in order to avoid potential substrate recognition problems caused by a fluorophore label attached to the substrate. Substrates and reaction products may be labelled with a fluorophore that is either charged or coupled with a charge imparting species when the fluorophore itself is uncharged and/or the not labelled form of the substrate is uncharged. Suitable fluorescent labels for use in the subject invention include those fluorophores that are useful in fluorophore assisted carbohydrate electrophoresis, such as 8-aminonaphthalene-1, 3, 6 -trisulphonic acid (ANTS), 1-amino-4-naphthalenesulphonic acid (ANSA), 1-amino-6, 8-naphthalenedisulphonic acid (ANDA), 7-amino-1, 3-naphthalenedisulphonic acid (Amido-G-Acid, AGA), 2-aminoacridone, lucifer yellow, and the like. A description of fluorophores suitable for use in labelling substrates and methods for their use can be found in U.S. patent application Ser. No. 07/483,043 (filed 16 Feb. 1990) and U.K. Patent Appln. Ser. No. GB/90/01448 (filed 20 Sep. 1990), published as PCT Appln. WO91/05256, P. Jackson, *Biochem. Journal,* 270:705-713 (1990), and P. Jackson, *Anal. Biochem.* 196:238-244 (1991). Fluorophore labelling of reaction products produced by the synthesis reaction may be conveniently carried out by drying the reaction mixture in a centrifugal vacuum evaporator, which will help stop the reaction, and then labelling the dried reaction mixture with a fluorophore label useful for fluorophore assisted carbohydrate electrophoresis.

For example, a first monosaccharide substrate, a nucleotide sugar substrate, and an appropriate carbohydrate-modifying enzyme may be incubated together so as to produce a disaccharide reaction product. The reaction mixture may then be labelled with a fluorophore and the reaction product separated from the reactants by fluorophore assisted carbohydrate electrophoresis. The separated disaccharide reaction product may then be mixed with a second carbohydrate-modifying enzyme and an appropriate new substrate, so as to produce a trisaccharide reaction product, which can be purified by fluorophore-assisted carbohydrate electrophoresis. Thus the subject invention greatly increases the convenience of in vitro enzymatic synthesis of carbohydrates by using fluorophore assisted carbohydrate electrophoresis to purify products of individual synthesis steps.

In one embodiment of the subject invention sequential enzymatic synthesis of carbohydrates of interest is facilitated by using immobilized carbohydrate-modifying enzymes and fluorophore labelled substrates so as to permit the repeated use of the enzymes and the rapid and convenient removal of reaction products from the individual synthesis reaction steps forming the complete synthesis pathway. The subject method of using carbohydrate. modifying enzymes immobilized in reaction matrix gels permits the synthesis reaction and the separation of the reaction product to be performed in a single step.

A series of reaction matrix gels may be set up in which each reaction matrix gel contains an immobilized carbohydrate-modifying enzyme. A substrate (or substrates) for the carbohydrate-modifying enzyme is added to the first reaction matrix gel, along with any co-factors that are required for the reaction. The reaction mixture is then allowed to incubate in the first reaction matrix gel so as to permit the carbohydrate-modifying enzyme to catalyze the reaction between the enzyme substrates or to catalyze a reaction affecting a single substrate. The reaction product is then removed from the reaction matrix gel by electrophoresis. After the reaction product has been removed, the reaction product may be transferred to a second reaction matrix gel containing a different immobilized carbohydrate-modifying enzyme that can use the reaction product being removed from the first reaction matrix gel as a substrate. The second reaction matrix gel may also contain appropriate cofactors and additional substrates for the second reaction. Similarly, the reaction product (or products) from the second reaction matrix gel may be removed by electrophoresis and transferred to additional reaction matrix gels in a like manner. Thus by employing multiple reaction matrix gels containing different immobilized carbohydrate-modifying enzymes in seriatim, desired carbohydrates may be obtained.

Carbohydrates that serve as substrates for the carbohydrate-modifying enzymes immobilized in the reaction matrix gels of the subject invention may be labelled with a fluorophore either before or during the addition of the substrate to the first reaction matrix gel. A substrate may be labelled during the addition of the substrate to the first reaction matrix gel by fluorophore labelling a portion of a substrate molecule that is transferred to a substrate molecule that has not been labelled in the reaction catalyzed by the first reaction matrix gel immobilized carbohydrate-modifying enzyme.

When carbohydrate synthesis is performed using carbohydrate-modifying enzymes immobilized on a reaction matrix gel, carbohydrate substrates are preferably labelled with a fluorophore before the substrate is added to the reaction matrix gel, i.e., pre-labelling. However, pre-labelling of a carbohydrate substrate may alter the activity of some carbohydrate-modifying enzymes. In order to avoid problems arising from altered enzyme activity, it may be necessary to pre-label some substrate molecules with an additional sugar or a spacer molecule attached to a point sufficiently distant from the point (or points) of substrate-enzyme interaction so as to avoid altering the interaction between enzyme and substrate. Suitable spacer molecules and methods of their chemical attachment to an appropriate sugar are known to those skilled in the art. The requirement of an additional sugar(s) or spacer molecule in pre-labelling may be obviated when the labelling is done following the enzyme-mediated synthesis or modification.

The carbohydrate-modifying enzymes employed in the subject carbohydrate synthesis and detection methods (and apparatus) may be immobilized in the reaction matrix gel. Most methods of immobilizing enzymes in a manner that permits the retention of a useful amount of carbohydrate-modifying activity are suitable for use in the subject methods and apparatus. The person of average skill in the art of bioconjugate chemistry will be aware of numerous techniques for immobilizing enzymes by linking the enzymes directly to a matrix, linking the enzyme to a matrix through cross-linking reagents and/or spacer techniques for immobilizing enzymes can be found, among other places in *Methods in Enzymology,* Volumes 135-137, Academic Press, San Diego, Calif. In a preferred embodiment of the subject invention, carbohydrate-modifying enzymes are immobilized by being embedded in the reaction matrix gel and are not covalently linked to the reaction matrix. Preferred reaction matrix gels for embedding carbohydrate-modifying enzymes are gels having a reaction matrix composed of polyacrylamide. The reaction matrix component of the gel is present in a sufficient density to effectively immobilize the carbohydrate-modifying enzyme of interest in the gel. Preferably the gels are composed of polyacrylamide having a concentration in the range of 20-36% and a cross-linking ratio (T/C) in the range of 35-38%. In general, higher concentrations of reaction matrix are required to immobilize smaller, i.e., lower molecular weight, carbohydrate-modifying enzymes. One method of embedding a carbohydrate-modifying enzyme in a reaction matrix gel is to place a buffer containing the carbohydrate-modifying enzyme of interest in contact with a reaction matrix gel and then applying an electric current so as to transfer the enzyme into the matrix by electrophoresis (the carbohydrate-modifying enzyme will not be "evenly" embedded in the reaction matrix gel, but will be concentrated at the buffer/gel interface); the use of a polyacrylamide gel for this method of embedding a carbohydrate-modifying enzyme is particularly preferred. Similarly, a carbohydrate-modifying enzyme may be embedded in a reaction matrix gel by placing a solution containing the carbohydrate modifying enzyme in contact with a stacking gel that is in contact with a reaction matrix gel. A stacking gel is a type of reaction matrix gel. A stacking gel is preferably composed of the same matrix material as the reaction matrix gel; however, the stacking gel has a lower concentration of the matrix material than other reaction matrix gels. When a stacking gel is employed, a solution containing the enzyme for embedding is placed in contact with the stacking gel; electrophoresis is used to move the enzyme through the stacking gel into the reaction matrix gel where the enzyme becomes immobilized at the stacking gel/reaction matrix gel interface. Another method of embedding a carbohydrate-modifying enzyme in a reaction matrix gel is to cast the reaction matrix gel so as to incorporate the carbohydrate-modifying enzyme of interest during the polymerization of the reaction matrix. Similarly, a stacking gel may be cast so as to incorporate a carbohydrate-modifying enzyme of interest.

Reaction components, including the carbohydrate-modifying enzymes, substrates, and other co-factors, may be added directly to the surface of a reaction matrix gel and allowed to incubate. The reaction components may be allowed to incubate at a given temperature for a sufficient time, either in situ when the gel is located in an electrophoresis apparatus, or incubated separately and then returned for electrophoresis. While being incubated in situ, the enzyme-catalyzed reaction may take place under static conditions or at a very low current density to allow sufficient time for the synthesis or modification of the desired carbohydrate. Incubation under low current density may have the advantage of avoiding substantial lateral diffusion of substrates and ultimately improving the resolution of carbohydrate bands in the gel.

The liquid phase confined within a reaction matrix gel may contain one or more buffers in order to optimize the activity and/or specificity of the carbohydrate-modifying enzyme immobilized in the reaction matrix. Buffers for use in maintaining enzyme activity are well known to the person of average skill in the art of biochemistry and can be found referring to publications describing the specific carbohydrate-modifying enzyme of interest.

Additional substrates may be added to a reaction matrix gel before, after, or during the addition of the carbohydrate substrate, or growing carbohydrate synthesis product, to the reaction matrix gel. Apparatus for performing the synthesis and/or measurement of carbohydrates may contain one or more means for delivery of substrate(s) (as well as other co-factors expended during the reaction) into reaction mixtures in reaction matrix gels and elsewhere. These delivery means include pumps, siphons, capillary tubing, and the like. The delivery means for introducing substrate molecules may be coordinated in an automated apparatus, typically employing one or more microprocessors and/or mechanical timing means so as to correlate the delivery of substrate(s) molecules to a reaction matrix gel (or other reaction mixture) with the delivery of the substrate that is a reaction product from a synthesis step to the reaction matrix gel (or other reaction mixture). The ability to produce such an apparatus is possessed by those skilled in the art of electrical and/or mechanical engineering.

The reaction product from an individual synthesis reaction step within a series of synthesis reactions in the subject invention may be removed from the reaction matrix by numerous methods based on the ability of the molecule to migrate in an electric field, i.e., electrophoresis. Thus the reaction product is necessarily charged or polar if it is to be separated from the other reactants by migration in an electric field. Uncharged carbohydrates may be used as substrates in the subject methods because the attachment of a charged fluorophore to the carbohydrate permits the molecule to migrate in an electric field, i.e., fluorophore-assisted carbohydrate electrophoresis may be employed.

Another aspect of the subject invention is to provide methods and apparatus for the measurement of the amount of a specific carbohydrate in a sample for analysis. The subject methods and apparatus for carbohydrate measurement involve the use of a carbohydrate-modifying enzyme immobilized, or not immobilized in a reaction matrix. Carbohydrates for detection are measured by the amount of reaction product produced by a carbohydrate-modifying enzyme, preferably an immobilized carbohydrate-modifying enzyme. Whereas conventional assays may only be performed once, a significant advantage of embodiments of the invention employing immobilized carbohydrate-modifying enzymes is to provide for multiple measurements from the same enzyme preparation.

Carbohydrate measurement assays of the subject invention involve the step of incubating a solution suspected of containing a carbohydrate for detection with a carbohydrate-modifying enzyme selected to catalyze a reaction in which the carbohydrate for detection is a substrate. Detection of the carbohydrate is made on the basis of observing changes in the structure of the carbohydrate for detection as determined by fluorophore-assisted carbohydrate electrophoresis. The choice of carbohydrate-modifying enzyme will vary in accordance with the identity of the carbohydrate of interest. Carbohydrate-modifying enzymes are selected so as to use the carbohydrate for detection as a substrate.

The reaction product of the subject carbohydrate assay methods is detected on the basis of the production of a fluorophore labelled reaction product. Suitable procedures for labelling carbohydrates with fluorophores can be found in publications describing fluorophore assisted carbohydrate electrophoresis. The timing of the step of fluorophore labelling of the reaction product may be varied in a variety of ways. The sample for analysis may be treated so that all carbohydrates present in the sample that have a free reducing end are labelled by the fluorophore. Another time for performing the labelling step is to fluorophore label all the components in a reaction mixture after the reaction has been allowed to proceed. The labelling of the reaction product may also be accomplished when a substrate molecule contains a fluorophore label on the carbohydrate portion.

For example, in one embodiment of the subject carbohydrate assay methods (and apparatus), a substrate molecule that is fluorophore labelled at the portion of the molecule that is transferred to a second substrate molecule may be added to the reaction matrix gel in conjunction with the sample for analysis, thereby avoiding the need to fluorophore label all carbohydrates that might be present in the sample for analysis. Thus, if the carbohydrate for detection is present in the sample for analysis, a fluorophore labelled carbohydrate is produced and may be detected by running an electric current through the reaction matrix gel so as to separate out the reaction product.

In another embodiment of the subject methods and apparatus for detecting specific carbohydrates, a sample for analysis may be treated so that any carbohydrates that are present in the sample are labelled with a fluorophore suitable for fluorophore assisted carbohydrate electrophoresis. Thus, the presence of a particular carbohydrate may be measured by monitoring for the production (and amount produced) of the expected fluorophore labelled reaction product. The production of the labelled reaction product may be detected by fluorophore assisted carbohydrate electrophoresis.

The fluorophore labelled reaction product produced in the subject assays for the presence of carbohydrates may be detected and measured by comparison with a standard and/or control. For example, fluorophore labelled samples may be split into two aliquots; one aliquot may then be added to a reaction matrix gel containing a carbohydrate. modifying enzyme and the second aliquot added to a reaction matrix gel without a carbohydrate-modifying enzyme.

Reaction matrix gels may take on a variety of shapes and be contained within a variety of holders. A suitable holder for a reaction matrix gel permits an electric current to flow through the reaction matrix gel. Particularly preferred shapes for reaction matrix gels are cylinders and thin sheets. Suitable holders for such reaction matrix gels with cylindrical or sheet shapes are widely available from commercial vendors and are commonly referred to as tube gel and slab gel electrophoresis apparatus. The subject apparatus for synthesis of carbohydrates may employ one or more reaction matrix gel holders. Additionally, a single reaction matrix holder may simultaneously hold a plurality of reaction matrix gels comprising different carbohydrate-modifying enzymes.

Apparatus for the synthesis of carbohydrates that comprises a plurality of reaction matrix gels may comprise means for transferring the reaction product(s) removed from one reaction matrix gel to another reaction matrix gel in seriatim. Suitable transfer means include pumps, siphons, capillary flow devices, and the like. Suitable transfer means also include the direct contact of different reaction matrix gels so that the reaction product from one reaction matrix gel enters a second reaction matrix gel containing a carbohydrate-modifying enzyme capable of using the first reaction matrix gel product as a substrate. When reaction matrix gel are in direct contact with each other, the carbohydrate-modifying enzyme employed in the synthesis may be located at the interface between the two gels.

It is of particular interest to provide reaction matrix gels containing immobilized carbohydrate-modifying enzymes in the form of cartridges. Cartridges of interest comprise a reaction matrix gel with an immobilized carbohydrate-modifying enzyme and a gel housing, i.e., a holder. The gel housing portion of the cartridge may be designed so as to be conveniently inserted into an apparatus for performing the subject methods of carbohydrate synthesis and/or carbohydrate measurement. Cartridges may be used to conveniently replace reaction matrix gels containing denatured carbohydrate-modifying enzymes and for rapidly changing the ability of an apparatus to synthesize or detect different carbohydrates. Cartridges may be stored under conditions that preserve the activity of the carbohydrate-modifying enzyme immobilized in the reaction matrix gel, e.g. refrigeration. By designing cartridges that may be easily inserted and removed from an apparatus for synthesizing carbohydrates of interest, the apparatus may be used to synthesize a wide variety of carbohydrates by simply inserting a cartridge containing the desired carbohydrate-modifying enzyme at the appropriate stage of synthesis. The housing of the cartridge has an input section designed to permit the input of the substrate, co-factors, and the like, that are required for synthesis. Similarly the housing of the cartridge has an output section designed to permit the outflow of the product of the reaction catalyzed by the carbohydrate-modifying enzyme immobilized in reaction matrix gel contained within the cartridge. Cartridges are also designed so as to permit an electric current to flow through the reaction matrix gel within the cartridge. A cartridge housing may be of an essentially tubular shape, with one end of the tube serving as the input section and the other end of the tube serving as the output section.

The voltage drop across a reaction matrix gel during electrophoresis and the amount of current flowing through may be varied during the subject carbohydrate synthesis methods and during the subject carbohydrate measurement methods. During the incubation stage of the subject methods, i.e., while the carbohydrate-modifying enzyme is catalyzing the structural changes of the substrate, the voltage drop across the reaction matrix gel may be reduced to permit extended incubation time. By employing appropriate control circuitry, electric power supply sources, and separation between reaction matrix gels, the voltage and current through each reaction matrix gel in the apparatus for carbohydrate synthesis may be varied independently of the voltage and current through other reaction matrix gels in the same synthesis apparatus.

The temperature of the reaction matrix gel may be raised and lowered while performing the subject methods of carbohydrate synthesis and measurement. Preferably, the temperature of the reaction matrix gel is at an optimum for biological activity of the carbohydrate-modifying enzyme immobilized in the reaction matrix gel during the substrate incubation stage. After the substrate incubation stage has been completed, the temperature of the reaction matrix gel may be changed so as to minimize the denaturation of the carbohydrate-modifying enzyme immobilized within the reaction matrix gel. Changes in the temperature of the reaction matrix gel may be accomplished by a variety of methods including, immersion in water baths, contacting the gel holder with a heating element, during the electric current flow through the reaction matrix gel, and the like. In an apparatus for performing the subject methods of carbohydrate synthesis or carbohydrate detection, means may be incorporated for controlling the temperature of reaction matrix gels. The temperature of individual reaction matrix gels within an apparatus may be varied independently of one another.

In addition to carbohydrate synthesis apparatus employing carbohydrate-modifying enzymes, the subject invention provides apparatus for synthesizing carbohydrates that does not comprise immobilized enzymes. This other type of apparatus is essentially the same as synthesis apparatus employing immobilized enzymes, except that the carbohydrate-modifying enzymes present in the apparatus are not immobilized.

Another aspect of the subject invention is to provide assays for detecting and/or quantitating the presence of carbohydrate-modifying enzymes that might be present in a sample for analysis. The carbohydrate-modifying enzyme assays provided employ a fluorescently labelled carbohydrate-substrate that is capable of being structurally modified by the activity of the carbohydrate-modifying enzyme being assayed; this substrate is referred to as the "assay substrate." The term "structurally modified" includes any change in the structure of the assay substrate, including the addition of atoms, the removal of atoms, and structural rearrangements. By selecting a suitable structure for the assay substrate, a wide variety of carbohydrate-modifying enzymes may be assayed. The carbohydrate portion of an assay substrate, i.e., the portion of the molecule other than the fluorophore label, may consist entirely of carbohydrate or be a glycoconjugate, e.g., a glycoprotein, glycolipid, glycosaminoglycan, or the like. Assay substrates are selected so as to be capable of being structurally altered by the carbohydrate-modifying enzyme of interest. The subject assays comprise the steps of contacting a sample for analysis with an assay substrate and detecting changes in the structure of the assay substrate by changes in the electrophoretic gel migration rate of the assay substrate. The assays also comprise the step of fluorophore labelling the assay substrate, either before or after the sample is contacted with the assay substrate, with a fluorophore suitable for use in fluorophore assisted carbohydrate electrophoresis.

The structural modifications of the assay substrate caused by the actions of the carbohydrate-modifying enzyme being assayed may be detected by a variety of means. A preferred method of assaying alterations in the structure of the substrate is by fluorophore-assisted carbohydrate electrophoresis.

Assay substrates may be prepared for detecting and quantifying the activity of carbohydrate-modifying enzymes that have not yet been discovered by producing substrates that have a structure of which at least a portion is similar or identical to the naturally occurring substrate for the enzyme of interest. For example, an enzyme that specifically hydrolyses a $\beta$ 1-4 linkage between D-fucose and D-glucose may be detected by using a substrate that is a polysaccharide having at least one $\beta$ 1-4 linkage between D-fucose and D-glucose (and is labelled with a suitable fluorophore).

Assays for carbohydrate-modifying enzymes using fluorophore-labelled carbohydrate substrates may be either quantitative or qualitative. Fluorophore-assisted carbohydrate electrophoresis permits the quantitative measurement of fluorescently labelled carbohydrates on the basis of band fluorescence intensity. Both quantitative and qualitative assays may be performed using similarly prepared samples for analysis containing substantially equal quantities of sample, fluorophore-labelled carbohydrate assay substrate, and other reaction reagents. Assays are preferably performed in parallel for equal periods of time. Performing assays for specific periods of time may require terminating the assay. The activity of a carbohydrate-modifying enzyme being assayed may be terminated in a variety of ways, including shifting the pH of the assay solution, adding chelating agents, incubation at high temperature, adding competitive inhibitors, adding denaturing agents, and separating the reaction mixture by electrophoresis. Carbohydrate-modifying enzyme assays are preferably performed with both negative and positive controls. Controls include performing assays without the addition of sample suspected of containing the enzyme of interest and assays known to contain the enzyme of interest. Quantitative carbohydrate-modifying enzyme assays may be performed to measure the rate at which an assay substrate is structurally altered by the carbohydrate-modifying enzyme of interest; rate measurements may require a measurement of changes in the amount of fluorescence of either the fluorophore-labelled carbohydrate substrate or the fluorophore-labelled carbohydrate substrate modification product as a function of time. Carbohydrate-modifying enzyme assays may also be performed in conjunction with standards of known quantity in order to determine the actual amount of substrate that is structurally altered by the carbohydrate-modifying enzyme of interest during a given assay. Standards may consist of the assay substrate before and/or after structural alteration by the carbohydrate-modifying enzyme being assayed The carbohydrate-modifying enzyme assays of the subject invention may employ various co-factors in the assay solution. Co-factors may include ions necessary for the activity of the enzyme. Co-factors may also include various inorganic groups and organic groups, including carbohydrates, that associate with the carbohydrate-modifying enzyme of interest so as to modify the fluorophore-labelled carbohydrate substrate.

An advantage of the carbohydrate-modifying enzyme assays of the subject invention is the ability to simultaneously perform assays for several different carbohydrate-interacting proteins within the same reaction mixture. In order to perform multiple assays simultaneously within the same reaction mixture, a plurality of assay substrates are added to the sample for analysis and the reaction mixture is subsequently analyzed by fluorophore assisted carbohydrate electrophoresis. When a plurality of fluorophore-labelled carbohydrate substrates are added to a single reaction mixture, the substrates differ in structure from one another and may be labelled with either the same or different fluorophores. Typically, one fluorophore-labelled carbohydrate substrate is added to the reaction mixture for each carbohydrate-interacting protein being assayed; however, assay substrates may be used that serve as substrates for more than one carbohydrate-interacting protein of interest.

When a plurality of carbohydrate-interacting proteins are being assayed simultaneously, the various assay substrates may be added individually or in solution(s) containing more than one assay substrate. Analysis of the results of assays for carbohydrate-modifying enzymes in which multiple fluorophore-labelled carbohydrate substrates are employed is preferably performed in conjunction with the use of computer programs for analyzing banding pattern changes caused by the presence of one or more carbohydrate-modifying enzymes of interest in samples for analysis.

Steps of the subject methods for synthesis of carbohydrates, detection of carbohydrates, and detection of carbohydrate-modifying enzymes are capable of being carried out by automated and semi-automated apparatus. Automation has numerous advantages over performing the subject methods manually. These advantages include improved reproducibility, improved accuracy, reduction in the amount of skilled manpower needed to achieve the same results, and the ability to perform the procedures 24 hours a day. The location of fluorophore labelled reaction products as they are removed from reaction matrix gels by electrophoresis in an apparatus may be rapidly and conveniently detected on the basis of fluorescence signal(s) as measured by a CCD, a fluorimeter, and the like. The fluorescence signal may be used to provide for the initiation of one or more steps by an automated apparatus, such as the transfer of a reaction product to a reaction matrix, the addition of reagents, the collection of samples, changes in temperature, changes in electric current flow, changes in voltage, and the like.

The subject invention also provides for kits for performing the subject carbohydrate-modifying enzyme activity assays, carbohydrate detection assays, and carbohydrate modifying enzyme mediated carbohydrate synthesis. Kits may include various combinations of the following items: fluorophores, fluorophore-labelled assay substrates, electrophoresis reagents, antibodies, CCDs, computer software for analysis of results, standards for analysis (including carbohydrate-modifying enzyme standards and modified assay substrates standards, i.e., substrates both before and after structural alterations by the carbohydrate-modifying enzyme of interest), gel fluorescence illumination equipment, chromogenic indicators, photographic equipment, reagent containers, cartridges containing carbohydrate-modifying enzymes immobilized on reaction matrix gels, carbohydrate substrates for use in synthesis, apparatus for performing the subject methods of carbohydrate synthesis, apparatus for performing the subject assays for carbohydrates, and apparatus for performing the subject assays for the detection of carbohydrate-modifying enzymes. Compounds included in kits are preferably provided in pre-measured portions and pre-mixed solutions so as to provide for reproducibility and minimize error in performing the subject syntheses and/or assays. Kits also preferably contain instructions. Instructions are directed to various steps in performing the subject assays and/or syntheses as described herein.

The invention having been described in the preceding paragraphs is illustrated by the following examples. The example are offered for the purpose of illustrating the subject invention and not limiting the invention.

EXAMPLE 1 Synthesis and analysis of lactose and N-acetyllactosamine with bovine milk galactosyltransferase Materials Bovine milk UDP-Gal : $\beta$-D-N-acetylglucosamine $\beta(1\rightarrow4)$ galactosyltransferase (EC 2.4.1.90/38/22) with a specific activity of 12 U/mg protein, UDP-Gal (disodium salt), D-glucose and N-acetylglucosamine (substrates), $\alpha$-lactalbumin, and cacodylic acid (sodium salt) were obtained from Sigma Chemical Co. (St Louis, Mo.).

Procedure

Enzyme-catalyzed synthesis reactions were carried out in Eppendorf vials containing 200 nmole of UDP-Gal, 100 nmole of Glc or GlcNAc and 100 mU of galactosyltransferase in 100 $\mu$L of 50 mM cacodylate buffer, pH 7.5, with 5 mM $MnCl_2$. $\alpha$-Lactalbumin (0.2 mg/ml) was included for the lactose synthesis reaction with D-glucose as the substrate. The reaction mixtures along with appropriate controls were incubated at 37° C. for 24 h. 1 mL of absolute ethanol was added to 10 $\mu$L aliquots of the mixtures and allowed to let stand in an ice-bucket for 1 h to stop the enzymic reaction, and dried in a centrifugal vacuum evaporator (c.v.e.). Five $\mu$L each of freshly prepared 8-aminonaphthalene 1,3,6-trisulfonic acid (ANTS, 0.2 M in 3:17 v/v acetic acid/water) and sodium cyanoborohydride ($NaCNBH_3$, 1.0 M in dimethylsulfoxide) solutions were added to the dried samples The solution was vortex mixed, centrifuged at $\sim$10,000 g (to ensure all the reactants were in the tip of the microcentrifuge tube) and incubated at 37° C. overnight ($\sim$16 h). The reaction mixture was then dried under vacuum in a c.v.e. at approximately 45° C. and dissolved in 200 $\mu$L of electrophoresis sample loading solution (12.5% glycerol in water) so that the concentration of labelled saccharide was a maximum of 50 pmole/$\mu$L (based on the initial amount of substrate used).

The fluorophore-labelled samples were subjected to PAGE using a standard type of electrophoresis apparatus (Bio-Rad Laboratories, Richmond, Calif.). The electrophoresis buffer used was based on Tris/HCl/glycine discontinuous system of Laemmli with the omission of SDS throughout. The polyacrylamide gel consisted of 36% (w/v) acrylamide containing 1% (w/v) N,N'-methylene-bis-acrylamide as a cross-linker. The dimension of the resolving gel was 80 mm high $\times$ 80 mm wide-$\times$ approximately 0.5 mm thick. A stacking gel (4%) was used and the sample wells were 7 mm wide. Two $\mu$L samples (containing a maximum of 100 pmole saccharide) were electrophoresed at a constant amperage of 20 mA for 90 min until the buffer front reached approximately 10 mm from the gel base. The gels were cooled to 5°-7° C. (during electrophoresis) by the surrounding lower electrode buffer stirred with a teflon-coated magnetic bar.

After the electrophoresis, the gel cassette was removed from the holder box, rinsed with water, and imaged directly using a cooled CCD camera system such as that described in U.S. Pat. No. 4,874,492. The gel contained six lanes. The migration of the product (fluorophore-labelled) lactose in the reaction mixture was observed as the major band in lane 1 and matched the control for the product run in lane 2. A small amount of unreacted glucose was identified in 1 in comparison with the control in lane 3. There was also another minor band, possibly due to spurious labelling of an impurity or an unidentified degradation product of the nucleotide, but well resolved from the major band, observed in lane 1. The synthesis of N acetyllactosamine was indicated by the presence of the major band in lane 4 which, by comparison with the reference product band in lane 5, appeared to have resulted from a complete conversion of the substrate, the latter being observed in lane 6. An unidentified but well resolved minor band was observed in lane 4; the band might have been caused by an impurity or a degradation product.

EXAMPLE 2 Enzymatic synthesis and sensitive analysis of carbohydrates using unnatural specificity of bovine milk galactosyltransferase The same procedure as described in Example 1 was followed except that UDP-GalNAc, UDP-Glc and UDP-GlcNAc (200 nmole each) were the nucleotide substrate, while GlcNAc (100 nmole) was used as the other substrate to exploit any unusual (unnatural) specificity of the bovine milk galactosyltransferase. All reactions were carried out at 37° C. for 64 h and in presence of α-lactalbumin (0.2 mg/mL). In order to remove the inhibitory UDP formed during the enzymatic synthesis, 55 nmoles of phosphoenolpyruvate with 5 U of rabbit muscle pyruvate kinase (EC 2.7.1.40) plus 40 nmoles of NADH and 17 U of lactate dehydrogenase were added to couple with the transferase activity. Hog muscle lactate dehydrogenase (EC 1.1.1.27) in glycerol solution was obtained from Boehringer-Mannheim Corp. (Indianapolis, Ind.) and all other reagents were from Sigma Chemical Co. (St Louis, Mo.). ANTS-labelling of the reaction mixtures as well as appropriate controls was continued for 19 h at 37° C. Electrophoresis of the labelled mixtures was performed in a 36% polyacrylamide gel and imaging of the gel with a CCD camera system was performed essentially as described in Example 1. A gel containing 7 lanes was run.

The enzymatic syntheses of GalNAc$\beta$(1→4)GlcNAc, Glc$\beta$(1→4)GlcNAc and GlcNAc$\beta$(1→4)GlcNAc were carried out in separate reaction mixtures; the reaction mixtures were run in lanes 2, 3 and 4, respectively. The band in lane 1 was the GlcNAc and lane 5 contained one of the products, GlcNAc$\beta$(1→4)GlcNAc (chitobiose), alone used as control references and processed under identical conditions as the reaction mixtures. The bands in lane 6 were the result of spurious labelling of the coupling enzyme reaction components. A faint band observed in lane 7 was produced by the UDP-GlcNAc, again prepared under the same conditions.

A small amount of the chitobiose (~4% of the substrate or 4 pmole) formed by the action of the bovine milk galactosyltransferase was identified at the top of lane 4, while most of the substrate (~96%) remained unreacted as compared with lanes 5 and 1 for GlcNAc$\beta$(1→4)GlcNAc and GlcNAc, respectively. This result was unexpected considering the previously reported results of M. M. Palcic and O. Hindsgaul, *Glycobiology*, 1: 205–209 (1991) that "simultaneously inverting the configuration at C-4 of Gal in UDP-Gal and replacing OH-2 by NHAc to produce UDP-GlcNAc gave a structure which was completely inactive when $\beta$GlcNAc-OR was used". It appeared that despite the relatively low activity of the bovine milk galactosyltransferase using UDP-GlcNAc as the nucleotide, it was still possible to detect the enzymatic activity under appropriate conditions provided that suitable methods and sensitive techniques such as those of the subject invention were employed. The results observed in lanes 2 and 3 confirmed this conclusion in that UDP-GalNAc and UDP-Glc were utilized in a quantitative manner because the Glc band was completely absent, perhaps due to somewhat longer reaction time of 64 h, albeit slowly, compared to that of 24 h in Example 1. Minor bands observed in lane 2 matched bands observed in lane 6 for the coupling enzyme reaction components, while the additional minor band (top position) in lane 3 might have originated from an impurity (similar to product in lane 2).

EXAMPLE 3 Rapid synthesis and analysis of an oligosaccharide using fluorophore-labelled chitobiose and human milk galactosyltransferase Essentially the same procedure as used in Examples 1 and 2 was followed, with the exceptions that only 1 nmole of pre-labelled ANTS-chitobiose and 2 nmoles of UDP-Gal were used as substrates, with 2 mU of human milk galactosyltransferase (Boehringer-Mannheim) and in absence of α-lactalbumin in a total reaction volume of 24 μL. The synthesis reaction was also carried out in the presence of coupling enzyme reaction components (10 nmoles of phosphoenolpyruvate, 2 U of pyruvate kinase, 20 nmoles NADH and 17 U of lactate dehydrogenase); the total volume of the reaction mixture was 33 μL (in separate microcentrifuge tubes). Parallel controls were run on the gel; these controls included every reactant, but the enzyme. All of the reactions were performed at room temperature (25° C.) for 2 h. The mixtures were then dried in a c.v.e. and then made up to 20 μL in electrophoresis sample loading solution. Subsequently, electrophoresis and imaging of the gel were conducted essentially as described in Example 1; 6 lanes were run. Lanes 1 and 3 corresponded to the synthesis reaction mixtures in the absence and in presence of the coupling components, respectively. Lane 6 was a duplicate of the sample in lane 3. The appropriate controls without the galactosyltrans. ferase were run in lanes 2 and 4, whereas lane 5 only contained the substrate (ANTS-labelled) chitobiose. A band at the top of lanes 1, 3 or 6 was produced by the quantitative formation of the oligosaccharide product Gal$\beta$(1→4)GlcNAc$\beta$(1→4)GlcNAc, as manifested by the absence of the substrate band in these lanes. An additional band observed at the bottom of all lanes, except for lane 5, may be due again to the nucleotide or an unidentified impurity.

EXAMPLE 4 Solid-phase enzymatic synthesis and analysis of an oligosaccharide in a tube gel using pre-labelled chitobiose as a typical substrate and human milk galactosyltransferase This experiment followed essentially the same procedure as used in Example 3, except that the enzymatic synthesis of the oligosaccharide product Gal$\beta$(1→4)GlcNAc$\beta$(1→4)GlcNAc was carried out on the solid phase of a 27% (w/v) polyacrylamide gel prepared in a glass tube (5 mm diameter × 90 mm long). Ten mU of the human milk galactosyltransferase was used with 0.5 nmole of the fluorophore-labelled acceptor substrate (ANTS-chitobiose) and 1 nmole of the nucleotide donor (UDP-Gal) in a total volume of 30 μL added on top of the resolving gel, with or without a 4% stacking gel (2 mm long). The tube gels with the reaction mixture and appropriate controls were incubated at 37° C. for 1 h only, and then electrophoresed at a current density of 1 mA/tube for approximately 4 h. The tubes were imaged by the same CCD camera system.

Tube 1 contained the reaction mixture in a tube gel prepared without a stacking gel, while tube 2 contained the same reaction mixture with the components added onto a stacking gel. Tube 3 contained a 2 µL aliquot of the reaction mixture taken directly from the reaction performed earlier in Example 3, and tube 4 contained 100 pmole of ANTS-chitotriose used as an appropriately suitable reference (the actual product was not available). Tube 5 contained a mixture of UDP-Gal (200 pmole) and ANTS-labelled chitobiose (100 pmole), the latter being the substrate used in the enzymatic synthesis of the oligosaccharide Gal$\beta$(1→4)chitobiose. The bands in tubes 1 and 2 both displayed the product band at the top of the gels; a minor difference between their position in tubes 1 and 2 was probably due to the variation of initial levels at which the reaction components were applied. The bands at the bottom of these gels were produced by unreacted ANTS-labelled chitobiose, consistent with the position of the unreacted substrate observed in tube 5.

EXAMPLE 5 Repeated use of a tube gel for rapid enzymatic synthesis and analysis of an oligosaccharide in the solid-phase The same tube gels of Example 4 were reused in essentially the same manner after extensive electrophoresis for another 11 h at 2.5 mA/tube to run off the earlier samples applied therein. The image of the tube gel banding patterns, was taken after electrophoresis at 1 mA/tube for 4.5 h with fresh reaction mixtures and appropriate controls in separate tubes, which were incubated at 37° C. for 1 h preceding the electrophoresis to allow for the synthesis reaction. Tube 1 had the same reaction mixture as in Example 4 but with a somewhat lower amount of human milk galactosyltransferase (8 mU). Tube 2 was used as a control having identical amounts of both substrates, but no enzyme was added, thus resulting in a single broad band produced by fluorophore-labelled substrate chitobiose. Tubes 3 and 4 were controls using 2 µL aliquots of the previously prepared product in Example 3 and the reference ANTS-chitotriose, respectively. The results from tube 1 indicated that the upper band was the enzymatic synthesis product Gal$\beta$(1→4)chitobiose, consistent with results in the other control lanes, thus demonstrating the reusability of tube gels for repeated synthesis of a typical oligosaccharide in the solid-phase.

Equivalents

It is to be noted that all publications and patent applications mentioned in this specification are indicative of the level of skill of those practicing the art to which this invention pertains. As well, all publications and patent applications are incorporated herein by reference to the same extent as if each individual publication or patent application was specifically and individually indicated to be incorporated by reference.

The foregoing written specification is considered to be sufficient to enable one skilled in the art to practice the invention. Indeed, various modifications of the above described modes of carrying out the invention which are obvious to those skilled in the field of carbohydrate chemistry, biochemistry, enzymology and glycobiology or related fields are intended to be within the scope of the following claims.

We claim:

1. A method for synthesizing a carbohydrate, said method comprising the steps:
    mixing a first carbohydrate substrate with a second substrate and a first carbohydrate-modifying enzyme whereby a first reaction mixture is produced,
    incubating said first reaction mixture, whereby a reaction product is produced,
    separating said first reaction product from said first reaction mixture by fluorophore assisted electrophoresis, whereby a separated first reaction product is produced.

2. A method according to claim 1, wherein said first reaction product is labelled with a fluorophore after said incubating step.

3. A method according to claim 1, said method further comprising the steps:
    mixing said separated first reaction product with a second carbohydrate-modifying enzyme that may used said first reaction product as a substrate, whereby a second reaction mixture is formed,
    incubating said second reaction mixture, whereby a second reaction product is produced,
    separating said second reaction product from said second reaction mixture by fluorophore assisted electrophoresis, whereby a separated second reaction product is produced.

4. A method according to claim 3, said method further comprising the step of mixing a third substrate with said second reaction mixture.

5. A method of synthesizing a carbohydrate, said method comprising the steps:
    adding a carbohydrate substrate to a first reaction matrix gel comprising a first carbohydrate-modifying enzyme specific for said carbohydrate substrate,
    incubating said gel under conditions permitting the interaction of said carbohydrate-modifying enzyme with said carbohydrate substrate so as to form a first reaction product, and
    removing said first reaction product from said matrix by fluorophore assisted carbohydrate electrophoresis.

6. A method according to claim 5 wherein said enzyme is immobilized in said gel by embedding.

7. A method according to claim 6, wherein said enzyme is immobilized at an interface between a stacking gel and said reaction matrix gel.

8. A method according to claim 5, said method further comprising the steps:
    transferring said first reaction product to a second reaction matrix gel comprising a second carbohydrate-modifying enzyme, wherein said first reaction product is a substrate for said second carbohydrate-modifying enzyme,
    incubating said second gel under conditions permitting the action of said second carbohydrate-modifying enzyme on first reaction product so as to form a second reaction product, and
    removing said second reaction product from said second gel by fluorophore assisted carbohydrate electrophoresis 9. An apparatus for synthesizing a carbohydrate, said apparatus comprising in functional combination:
    a first reaction matrix gel comprising a first carbohydrate-modifying enzyme capable of catalyzing a reaction with a carbohydrate substrate, whereby a first reaction product is produced, a means for introducing a carbohydrate substrate for said first carbohydrate-modifying enzyme into said gel, and a means for generating a voltage drop over said gel, wherein said voltage drop can separate the reaction product from said gel.

10. An apparatus according to claim 9, wherein said first enzyme is immobilized in said gel by embedding.

11. An apparatus according to claim 10, wherein said first enzyme is immobilized at an interface between a stacking gel and said reaction matrix gel.

12. An apparatus according to claim 9, said apparatus further comprising in functional combination, a second reaction matrix gel comprising a second carbohydrate-modifying enzyme, wherein said first reaction product is a substrate for said second carbohydrate-modifying enzyme, a means for transferring a first reaction product from said first reaction matrix gel to said second reaction matrix gel, and a means for generating a voltage drop over said second reaction matrix gel, wherein said voltage drop can separate said second reaction product from said gel.

13. A method of measuring the presence of a carbohydrate in a test sample, said method comprising the steps:

adding a test sample suspected of containing a carbohydrate of interest to a reaction matrix gel comprising a carbohydrate-modifying enzyme, wherein said carbohydrate of interest is a substrate for said first carbohydrate-modifying enzyme, incubating said gel under conditions permitting catalyzation of a reaction by said carbohydrate-modifying enzyme on said carbohydrate of interest so as to form a reaction product, and removing said reaction product from said gel by fluorophore assisted carbohydrate electrophoresis.

14. A method according to claim 13, wherein said enzyme is immobilized in said gel by embedding.

15. A method according to claim 14, wherein said enzyme is immobilized at an interface between said reaction matrix gel and a stacking gel.

16. A method according to claim 13, said method further comprising the step, detecting the reaction product separated from said gel.

17. A method according to claim 13, said method further comprising the step, labeling carbohydrates present in said sample with a fluorophore.

18. A cartridge comprising in functional combination, a reaction matrix gel, a carbohydrate-modifying enzyme, wherein said enzyme is immobilized in said gel, and a gel housing containing said gel.

19. A cartridge according to claim 18, wherein said enzyme is embedded in said reaction matrix gel.

20. A method of detecting a carbohydrate-modifying enzyme present in a sample for analysis, said method comprising the steps, contacting said sample for analysis with a fluorophore-labelled assay carbohydrate substrate, and detecting a structural modification of said assay substrate catalyzed by said enzyme.

21. A method according to claim 20, wherein said detecting step is fluorophore assisted carbohydrate electrophoresis.

22. A kit for synthesizing a carbohydrate, said kit comprising:

a carbohydrate modifying enzyme, a first carbohydrate substrate, a second substrate, and a fluorophore label suitable for use in fluorophore-assisted carbohydrate electrophoresis.

23. A kit for detecting a carbohydrate of interest in a sample for analysis, said kit comprising:

a reaction matrix gel, wherein said gel comprises an immobilized carbohydrate modifying enzyme having carbohydrate modifying activity for said carbohydrate of interest, and a fluorophore label suitable for use in fluorophore-assisted carbohydrate electrophoresis.

24. A kit for detecting a carbohydrate-modifying enzyme present in a sample for analysis, said kit comprising:

a carbohydrate substrate, and a fluorophore label for use in fluorophore assisted carbohydrate electrophoresis.

* * * * *